United States Patent [19]

Williams et al.

[11] Patent Number: 4,761,379

[45] Date of Patent: Aug. 2, 1988

[54] BIOLOGICAL SPECIMEN COLLECTION DEVICE

[75] Inventor: Edward L. Williams, West Milford; Larry A. Franchore, Sparta, both of N.J.

[73] Assignee: Becton, Dickinson and Company, Franklin Lakes, N.J.

[21] Appl. No.: 639,279

[22] Filed: Aug. 9, 1984

[51] Int. Cl.$^4$ ............................................. C12M 1/24
[52] U.S. Cl. .................................. 435/296; 435/810; 422/102; 215/100 R; 128/760; 206/569
[58] Field of Search ............... 435/292, 293, 294, 296, 435/299, 810; 422/99, 102; 215/100 R; 128/760, 763; 206/569

[56] References Cited

U.S. PATENT DOCUMENTS

| | | | |
|---|---|---|---|
| 3,518,164 | 6/1970 | Andelin et al. | 435/296 X |
| 3,890,204 | 6/1975 | Avery | 435/810 X |
| 3,968,012 | 7/1976 | Jones | 435/810 X |
| 4,038,148 | 7/1977 | Miller et al. | 435/810 X |
| 4,283,498 | 8/1981 | Schlesinger | 435/296 |
| 4,335,730 | 6/1982 | Griffin | 422/102 X |
| 4,364,903 | 12/1982 | Bittings | 422/102 X |
| 4,443,896 | 4/1984 | Porat et al. | 422/102 X |
| 4,576,185 | 3/1986 | Proud et al. | 128/760 |
| 4,589,548 | 5/1986 | Fay | 435/296 X |

Primary Examiner—Alan Cohan
Attorney, Agent, or Firm—Robert P. Grindle

[57] ABSTRACT

A biological specimen collection device comprises a specimen receptacle having a closed first end and an open second end. A removable conduit is provided for introducing a biological specimen into the receptacle and is connected to the second end of the receptacle. A base removably receives the first end of the receptacle and supports the receptacle in a substantially vertical position. A cap is removably connected to the base, this cap adapted to provide a liquid seal between the cap and the open second end of the receptacle. The cap is maintained in a protective environment during introduction of the biological specimen into the receptacle. Access is permitted to the cap after the specimen has been collected for subsequently capping the open end of the receptacle with its contents.

35 Claims, 5 Drawing Sheets

BIOLOGICAL SPECIMEN COLLECTION DEVICE

BACKGROUND OF THE INVENTION

1. Field of the Invention

The present invention relates to a biological specimen collection device, and more particularly, concerns such a device which may be employed in the collection of sputum.

2. Description of the Prior Art

In order to perform various tests on biological specimens, particularly biological fluids or fluid-based specimens such as urine, blood, sputum and the like, these specimens must first be collected in a suitable container. Primarily the collection container should have the appropriate configuration and features to not only conveniently collect the biological specimen, but also allow the specimen to be easily and properly transported to the area of test or analysis. While the configuration of the specimen collection device should be designed and fabricated to make the collection procedure convenient, handling of the specimen collection device prior to, during and subsequent to its use is a major concern.

For example, if the specimen to be collected is sputum, the patient from whom the sputum is to be collected is often times suspected of having, and indeed does have, a pulmonary infection, disease or other pulmonary disorder. The specimen collection device should be sterile prior to the collection of the biological specimen so that the testing and analysis of the collected specimen accurately portrays the condition of the patient. Handling of the specimen collection device during the specimen collection procedure and subsequent transport of the specimen should be considered in the design and fabrication thereof so that the risk of spreading infection is minimized.

U.S. Pat. No. 3,518,164 to Andelin et al. takes into account many of the above-mentioned concerns. The Andelin et al. collection system further provides a graduated elongated specimen receptacle which may also be used as a centrifuge and diagnostic test tube. By collecting the specimen directly into such elongated receptacle, there is no need to transfer the specimen to another container for subsequent testing and analysis. It is, of course, apparent that eliminating this transfer step should increase the safety of handling the specimen container and thereby minimize the risk of spreading infection of other contamination. The Andelin et al. collection system, however, relies upon an outer protective body which is preferably made of a rigid material which supports the specimen collection funnel and contributes toward supporting the elongated receptacle in a vertical position. This outer protective body adds weight, bulk, expense and user complexity to the specimen collection system which, collectively, could be somewhat disadvantageous.

An improved biological specimen collection and transport system is disclosed in U.S. Pat. No. 4,283,498 to Schlesinger. While Schlesinger includes many elements and features similar to Andelin et al., Schlesinger further includes a flexible outer protective covering enclosing the specimen receptacle. Schlesinger indicates that this protective covering prevents contamination of the outer surface of the specimen receptacle by a biological specimen during introduction of that specimen into the receptacle. Further, Schlesinger includes a cap removably attached to the periphery of the receptacle. This cap is included so that it may be placed on top of the open end of the receptacle after the biological specimen has been collected. Due to the positioning of the cap of Schlesinger's invention, it is possible that the cap, when detached from the periphery of the receptacle, could become contaminated. Subsequent placement of this cap on top of the receptacle after use could then contaminate the contents inside the receptacle, thus producing a possibility of distorted testing and analysis.

Therefore, there is still a need for improvements in biological specimen collection devices to make these devices more convenient to use and less expensive to manufacture, while assuring that the handling of these devices prior to, during and subsequent to the specimen collection will be performed with minimal risk of spreading infection to the users or contaminating the contents collected therein.

SUMMARY OF THE INVENTION

The biological specimen collection device of the present invention comprises a specimen receptacle having a closed first end and an opened second end. Removable conduit means introduces a biological specimen into the receptacle and is connected to the second end of the receptacle. Base means removably receives the first end of the receptacle for supporting the receptacle in a substantially vertical position. Cap means is removably connected to the base means. This cap means is adapted to provide a liquid seal between the cap means and the open second end of the receptacle. Means associated with the base maintains the cap in a protective environment prior to use of the device. This maintenance means also permits access to the cap for capping the open end of the receptacle with its contents.

In a preferred embodiment of the present invention, the collection device is a sputum collection device and comprises an elongated, cylindrically shaped sputum receptacle having a conically shaped, closed bottom end and an open top end. A funnel includes a relatively wide sputum receiving portion and a passage tube to which the receptacle is removably connected so that the tube communicates with the inside of the receptacle through its open end. A base removably receives the closed bottom end of the receptacle for supporting the receptacle in a substantially vertical position. The base further includes a recess therein extending inwardly from the bottom support surface. A cap, adapted to engage the open top end of the receptacle after the funnel is removed, is protectively positioned in the recess. Sealed over the recess to maintain the cap in a substantially contamination-free environment is a peelable, protective cover. This cover is removable to permit access to the cap for capping the open end of the receptacle with its contents.

In accordance with the principles of the present invention, a convenient to use and low cost biological specimen collection device is provided. The collection device of the present invention is designed for ease of handling to minimize the risk of spreading infection by various personnel involved in the procedures of collecting, testing and analyzing the specimens. Further, the collection receptacle of the present invention may be utilized as a centrifuge tube thereby eliminating a transfer step between collection receptacle and a different centrifuge tube. In addition, a cap is provided for the collection receptacle to seal the receptacle with its contents after the collection procedure has been completed. This cap is stored, during handling and shipment in a hidden recess. Two advantageous features are thus provided: (1) the cap is protectively stored out of the way of the functional use of the specimen receptacle during the specimen collection procedure, and therefore does not require functional space for such storage; and (2) the cap may be preferably maintained in a sterile or containation-free environment until the specimen has been collected, whereby the cap may then cover the open end of the receptacle. In an embodiment of the present invention, once the cap is exposed for use, the open end of the receptacle may be placed into engagement into the cap without the cap being touched. This, of course, eliminates the risk of contamination of the cap as it is placed on top of the open end of the receptacle with its contents therein. Other advantages and features of the present invention will become more apparent upon reading the ensuing detailed description of the present invention.

DETAILED DESCRIPTION

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Adverting to the drawings, and FIGS. 1-4 in particular, there is illustrated the preferred biological specimen collection device 10. This device is useful for the collection of biological specimens such as urine, sputum, blood and the like. This collection device includes an elongated, preferably cylindrically shaped, specimen receptacle 12. One end of receptacle 12 is a closed end 14 and is preferably conically shaped with inwardly tapering side walls 15. At the other end of receptacle 12, there is an opening 16 which commmunicates with the interior of the receptacle so that the specimen may be collected therein. Around opening 16 is an external thread 18 which facilitates the closure of the threaded cap, as described hereinafter. A series of graduation marks 19 may be included on the peripheral surface of the receptacle to indicate volume; other indicia may also be marked on the receptacle as may be desired.

As can be seen in the drawings, the elongated nature of receptacle 12 makes it useful as a centrifuge tube so that the specimen, once collected, need not be transferred to a different container for centrifugation. To this end, receptacle 12 is constructed from material with sufficient structural properties so that it may be centrifuged at appropriate speeds in standard centrifuges. Rigid polymeric materials such as polypropylene, polyethylene, polystyrene and the like are suitable materials for centrifuging purposes. Other materials may also be employed depending upon the nature of the specimen to be collected and subsequent testing and analysis.

Figure 1:
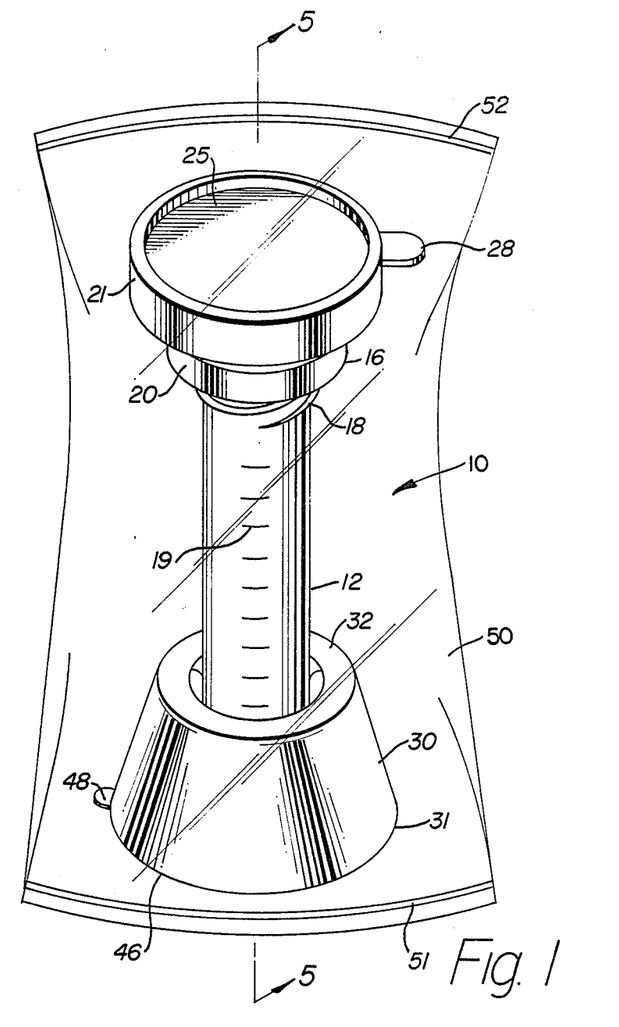
FIG. 1 is a perspective view of the preferred biological specimen collection device of the present invention illustrated as packaged.
Figure 2:
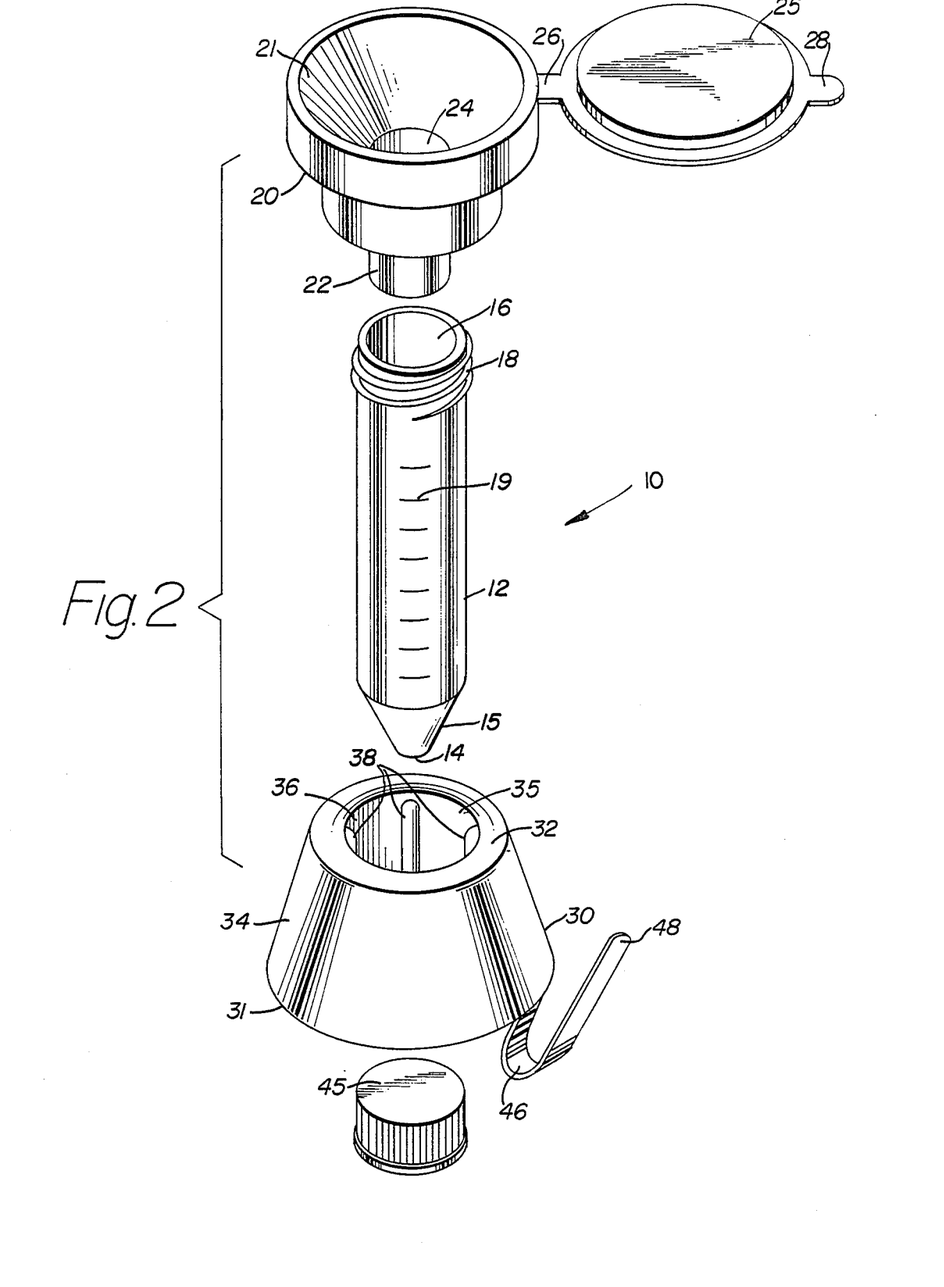
FIG. 2 is an exploded, perspective view of the preferred biological specimen collection device of the present nvention.

A funnel 20 includes a relatively wide specimen receiving portion 21 into which the specimen is deposited when being collected from the patient. Communicating with this wide receiving portion is a passage tube 22 which has a passage way 24 extending therethrough. Tube 22 slidably, but preferably snugly, fits inside opening 16 at the top end of receptacle 12. In this fashion, tube 22 and passageway 24 communicate with the inside of receptacle 12 so that the funnel can serve its function. The fit between tube 22 and the open end of the receptacle allows for ready removal of the funnel after the specimen has been collected.

It is preferred that funnel 20 include a cover 25 to provide a sealing closure over receiving portion 21 of the funnel. In the preferred embodiment of this invention, cover 25 is connected to funnel 20 by virtue of a hinge 26.

Funnel 20 and cover 25 may be fabricated of plastic, glass or other materials, but are preferably made of plastic, polypropylene, polyethylene, polystyrene or the like. When plastic is used for the funnel and cover, hinge 26 may be integrally formed between the funnel and the cover so as to provide the so-called living hinge. A finger tab 28 is provided on cover 25 to facilitate the lifting a closure of the cover with respect to the funnel.

A base 30 is included in the present biological specimen collection device in order to receive closed bottom end 14 of the receptacle and to support the receptacle in a substantially vertical position, particularly when the specimen is being collected. As seen more clearly in FIGS. 3 and 4, taken in conjunction with FIG. 2, base 30 includes a bottom support surface 31, a top surface 32 and side walls 34 interconnecting the top and bottom surfaces of the base. In the preferred embodiment of this base, it is cylindrically shaped so that side wall 34 is one continuous side wall around the periphery of the base. An opening 35 is formed through top surface 32 and is sized to receive the outside diameter of receptacle 12 so that the receptacle may be supported in the base. Communicating with opening 35 is a bore 36 which is also sized to receive the outside diameter of receptacle 12 therein. Bore 36 extends into the base from top surface 32 in a direction substantially perpendicular to bottom surface 31 of the base. Thus, receptacle 12 may be supported in the base in a substantially vertical position as seen by briefly referring to FIGS. 1 and 5.

Figure 3:
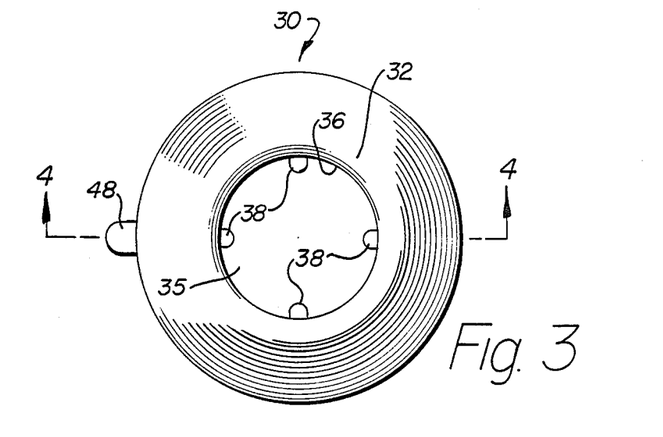
FIG. 3 is a top plan view of the preferred base for supporting the specimen receptacle of the present invention.
Figure 4:
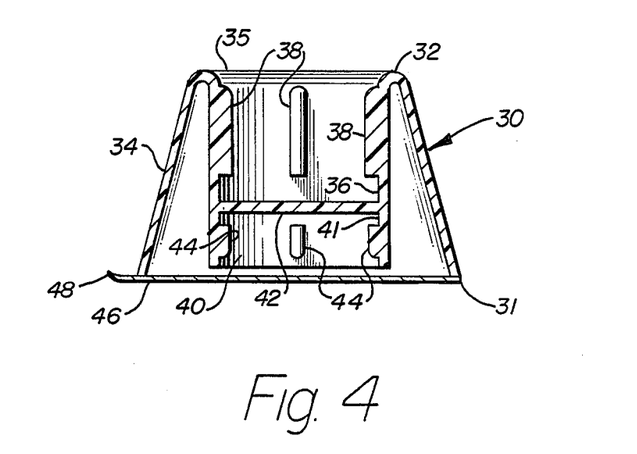
FIG. 4 is a cross-sectional view of the base taken along line 4—4 of FIG. 3.

As illustrated particularly in FIGS. 3 and 4, bore 36 includes a plurality of spaced inwardly extending locking ribs 38. These locking ribs are formed against the inside surface defined by bore 36 of the base and are adapted to firmly hold the receptacle in position once the receptacle has been inserted in the base. It is preferred that bore 36 have a circular cross-section to be compatible with the preferred cylindrical shape of receptacle 12.

Extending inwardly into base 30 from bottom support surface 31 is a recess 40. This recess is defined by a bore or a cylindrical side wall 41 and a substantially horizontal wall 42 which, in the embodiment being described, separates recess 40 from bore 36. Whereas bore 36 is adapted to receive receptacle 12, recess 40, defined by bore 41, is adapted to receive a cap 45, as more clearly seen by referring briefly to FIG. 5. In order to facilitate the firm holding of cap 45 in position within recess 40, a plurality of spaced inwardly extending locking ribs 44 is provided to engage the cap. Locking ribs 44 are similar in nature to the previously described locking ribs 38, and are formed against the inner surface of bore 41 of the base.

While base 30 may be made of many materials, depending upon choice, design and use of the present device, the material of preference is rigid plastic. Moreover, it is preferred that base 30 be molded as an integral, unitary structure, in order to render its fabrication easy and inexpensive. As an integral, one piece structure, locking ribs 38 and 44 are also formed together with the other structural elements of the base.

Figure 5:
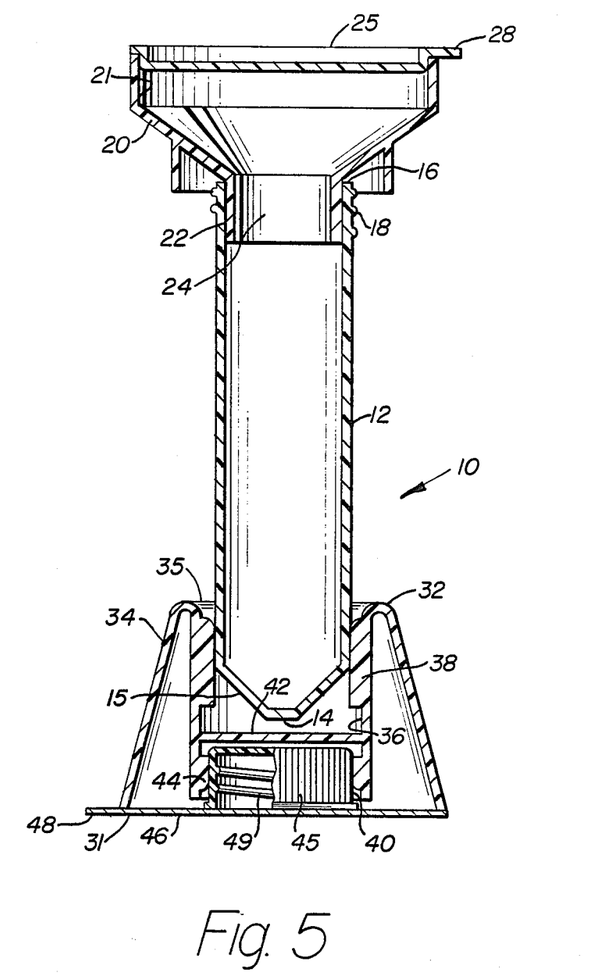
FIG. 5 is a cross-sectional view of the completely assembled biological specimen collection device taken through line 5—5 of FIG. 1.

Referring now to FIG. 5 which illustrates cap 45 protectively maintained within recess 40, it can be seen that the entire bottom support surface of base 30 has been covered. In the specific embodiment being described, a peelable, flexible, protective cover 46 is sealed around the entire periphery of the bottom surface of the base. Various adhesives, cement or appropriate fastening techniques may be employed to effectuate this seal. A finger tab 48 is provided so that the user may peal cover 46 from the bottom surface of the base when the cap should be exposed for capping the receptacle. It is one purpose of cover 46, together with recess 40, to enclose and maintain cap 45 in a substantially contamination-free environment prior to use of the biological specimen collection device of the present invention. To this end, and inasmuch as all of the elements of this collection device are preferably sterilized as a packaged unit, protective cover 46 may be fabricated of a suitable paper material which will allow cap 45 to be sterilized using typical and well-known sterilizing techniques for medical products. At the same time, this paper or other material for cover 46 should prevent the ingress of microorganisms into cavity 40 where they would contaminate cap 45 before use. While the present invention is herein described with protective cover 46 as a preferred feature, it is within the purview of the present invention to eliminate this protective cover. Cap 45 is then protected, prior to use of the device, by its position within recess 40. Cap 45 is sized to fit on top of opening 16 of the specimen receptacle and preferably includes an internal thread 49 which mates with thread 18 around open end 16 of the specimen receptacle. Cap 45 is preferably made of rigid plastic, such as polypropylene, polyethylene, polystyrene or the like.

The assembled biological specimen collection device may be packaged in a removable, flexible outer protective package 50 to facilitate sanitary handling both prior to and during the specimen collection procedure. Package 50 may be a transparent, flexible thermoplastic bag which may be appropriately sealed along seal lines 51 and 52. When opening package 50, it is preferred to cut the package at or near seal line 51 thereby leaving the remainder of package 50 substantially intact for further use during the specimen collection procedure as described below.

Figure 6:
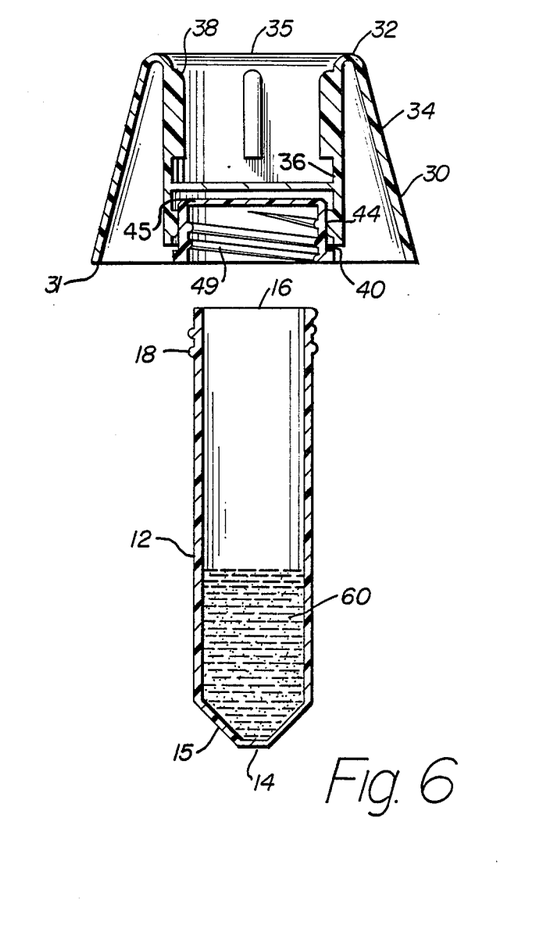
FIG. 6 is a cross-sectional view of some components of the biological specimen collection device illustrated in use after the specimen has been collected in the receptacle which is to be capped.

In use, biological specimen collection device 10 is assembled as illustrated in FIG. 5. Specimen receptacle 12 is slidably and firmly positioned with its closed bottom end 14 inserted into bore 36 of base 30. Locking ribs 38 contribute to firmly holding the specimen receptacle in a substantially vertical position, as illustrated. Funnel 20 is removably positioned so that tube 22 is inserted inside opening 16 at the top end of receptacle 12. At this time, prior to specimen collection, cap 45 is maintained in a substantially contamination-free enviroment within recess 40 inside base 30. Protective cover 46 is intact in sealed condition on the bottom support surface of base 30. In order to collect the biological specimen, such as sputum, cover 25 is lifted by virtue of finger tab 28 whereupon the specimen is deposited in wide receiving portion 21 of the funnel. The specimen passes through passageway 24 of the funnel and opening 16 of the specimen receptacle whereupon the specimen is deposited into the interior of the receptacle. When the specimen has been collected, cover 25 is repositioned to provide a sealing closure over the receiving portion of the funnel. It is preferred, at this stage of the procedure, to replace flexible package 50 over the entire specimen collection device. While lifting the device by grasping around the outside of the flexible package, and maintaining receptacle 12 in a substantially vertical position, the laboratory technician then grasps finger tab 48 and peels protective cover 46, if included on the device, from the bottom surface of the base, thereby exposing cap 45. The receptacle is removed from the base and the funnel is removed from the receptacle. As seen in FIG. 6, receptacle 12 with specimen 60 therein, and while maintained substantially vertically, is positioned under base 30 and more directly under cap 45. Locking ribs 44 hold the cap in a fixed position inside recess 40. Moving the receptacle upwardly into the cap will cause open end 16 to come in contact with the interior of the cap. A turning motion will cause thread 18 at the open end of the receptacle to become engaged with the thread 49 in the interior of the cap. Once in position, cap 45 may be appropriately tightened at the top end of the receptacle with its contents therein. Inasmuch as receptacle 12 may be centrifuged, at this time the specimen may be transported directly to the centrifuge without the need for transfer to a different container or tube.

Thus, the present invention provides a biological specimen collection device which is easy to use, inexpensive to manufacture and may be conveniently handled so as to minimize the spread of infection during and subsequent to the specimen collection procedure. Furthermore, the present specimen collection device conveniently stores the receptacle cap in a protective environment until the cap is needed to seal the contents of the specimen receptacle.

What is claimed is:
1. A biological specimen collection device comprising:
   an elongated specimen receptacle having a closed bottom end and an open top end;
   a funnel having a relatively wide specimen receiving portion and a passage tube to which said receptacle is removably connected so that said tube communicates with the inside of said receptacle through its open end;
   a base for removably receiving the closed bottom end of said receptacle for supporting same in a substantially vertical position;
   a cap removably connected to said base, said cap adapted to engage the open top end of the said receptacle after said funnel is removed therefrom to provide a liquid seal between the cap and the receptacle; and means associated with the base for maintaining the cap in a protective environment prior to use of the device and for permitting access to the cap for capping the open end of the receptacle with its contents.

2. The device of claim 1 wherein said funnel further includes a cover removably connected thereto to provide a sealing closure over the receiving portion of the funnel.

3. The device of claim 2 wherein said cover is hingedly connected to the funnel.

4. The device of claim 1 wherein the closed bottom end of said receptacle is conically shaped.

5. The device of claim 1 wherein said receptacle is threaded at its open end and said cap includes a mating thread to engage the thread of said receptacle to provide said liquid seal between the cap and the receptacle.

6. The device of claim 1 wherein said base includes a bottom support surface, a top surface and side walls interconnecting said top and bottom surfaces.

7. The device of claim 6 wherein said base further includes an opening through said top surface sized to receive the receptacle therethrough so that the receptacle is supported in the base.

8. The device of claim 7 wherein said base further includes a bore communicating with said opening, said bore sized to receive the receptacle therein and extending into said base from said top surface in a direction perpendicular to said bottom surface so that said receptacle is supported therein in a substantially vertical position.

9. The device of claim 8 wherein said bore includes a plurality of spaced, inwardly extending locking ribs to engage the receptacle and facilitate its support in the base.

10. The device of claim 9 wherein said receptacle is cylindrically shaped and said bore has a circular cross-section.

11. The device of claim 6 wherein said means for maintaining includes a recess extending inwardly from the bottom support surface of the base inside which said cap is removably maintained.

12. The device of claim 11 wherein said recess includes a plurality of spaced, inwardly extending locking ribs to engage the cap and facilitate its maintenance in the base.

13. The device of claim 11 wherein said means for maintaining further includes a removable protective cover positioned over said recess and said cap maintained therein.

14. The device of claim 13 wherein said protective cover is peelably connected to the bottom support surface of said base.

15. The device of claim 14 wherein said cap is sterilized and said protective cover maintains the sterility of the cap prior to use of the cap.

16. The device of claim 1 further including a removable, flexible outer protective package enclosing the receptacle, funnel, base and cap until ready for use.

17. The device of claim 16 wherein said receptacle, funnel, base and cap are sterilized and said outer protective package maintains said sterility until the enclosure provided by said package is compromised.

18. A biological specimen collection device comprising:
a specimen receptacle having a closed first end and an open second end;
removable conduit means for introducing a biological specimen into the receptacle connected to the second end of said receptacle;
base means for removably receiving the first end of the receptacle for supporting same in a substantially vertical position;
cap means removably connected to said base means, said cap means adapted to provide a liquid seal between the cap means and the open second end of said receptacle; and
means associated with the base means for maintaining the cap means in a protective environment prior to use of the device and for permitting access to the cap means for capping the open end of the receptacle with its contents.

19. A sputum collection device comprising:
an elongated, cylindrically shaped sputum receptacle having a conically shaped, closed bottom end and an open top end;
a funnel having a relatively wide sputum receiving portion and a passage tube to which said receptacle is removably connected so that said tube communicates with the inside of said receptacle through its open end, said funnel including a hingedly connected cover to provide a sealing closure over the receiving portion of the funnel;
a base having a bottom support surface, a top surface and side walls interconnecting said top and bottom surfaces, and including a bore having a circularly shaped cross-section sized to receive the receptacle therein and extending into the base from the top surface in a direction substantially perpendicular to the bottom surface so that said receptacle is supported therein in a substantially vertical position, said base further including a recess therein extending inwardly from the bottom support surface;
a cap adapted to engage the open top end of the receptacle after the funnel is removed therefrom to provide a liquid seal between the cap and the receptacle, said cap being positioned within said recess; and
a peelable, protective cover sealed over said recess to maintain said cap in a substantially contamination-free enviroment prior to use of the device, said protective cover being removable to permit access to the cap for capping the open end of the receptacle with its contents.

20. The device of claim 19 which further includes a removable, flexible outer package to provide a protective enclosure for the device until the device is ready for use.

21. An apparatus for collecting sputum comprising:
a sputum container having an open end and a closed end;
a funnel including a mouth at one end and a discharge portion at the other end, said discharge portion being removably attachable to said container to establish fluid communication between said funnel and said container;
a cap for removably covering the container opening; and
a short base remote from said funnel and having a top which includes a recess for receiving the closed end of said container to support at least a portion of said container above said base, said container being the sole structural, interconnection between said funnel and base, said base includes a chamber with an opening at its lower end, and means mounted within said chamber for releasably holding said cap with the inside of said cap facing said chamber opening to enable said cap to be attached to said container and cover the open end of said container when said container is introduced generally axially into said base and be properly seated on and removed by said container without direct handling when said container is withdrawn from said base.

22. The apparatus of claim 21 in which said container is elongate.

23. The apparatus of claim 21 in which said container is a tube.

24. The apparatus of claim 23 in which said tube includes graduated indicia thereon.

25. The apparatus of claim 23 in which said tube includes thread means proximate the open end thereof and said cap includes complementary thread means for engaging the thread means of said tube to cover said tube.

26. The apparatus of claim 21 further including an upper lid for selectively closing the mouth of said funnel.

27. The apparatus of Claim 26 in which hinge means interconnect said upper lid and said funnel.

28. The apparatus of claim 27 in which said funnel, hinge means and upper lid are integrally interconnected.

29. The apparatus of claim 21 in which said means for holding includes means for gripping the periphery of said cap.

30. The apparatus of claim 29 in which said means for gripping includes a plurality of radial projections spaced about said chamber and extending inwardly from the wall of said chamber to provide a friction fit between the periphery of said cap and said projections.

31. The apparatus of claim 21 in which said means for holding locates said cap centrally within said base.

32. The apparatus of claim 21 in which said cap is translucent.

33. The apparatus of claim 21 in which said cap is opaque.

34. An apparatus for collecting sputum comprising:
a tubular sputum container having an open end and a closed end;
a funnel including a mouth at one end and a discharge portion at the other end, said discharge portion being removably attachable to said container to establish fluid communication between said funnel and said container;
a cap for removably covering the container opening; and
a short base remote from said funnel and having a top which includes a recess for receiving the closed end of said container to support at least a portion of said container above said base, said container being the sole structural interconnection between said funnel and base, said base including a chamber with an opening at its lower end, and means mounted within said chamber for releasably gripping the periphery of said cap with the inside of said cap facing said chamber opening to enable said cap to engage and cover the open end of the container when said container is introduced generally axially into said base and be properly seated on and removed by said container without direct handling when said container is withdrawn from said base.

35. An apparatus for collecting sputum comprising:
a tubular sputum container having an open end and a closed end;
a funnel including a mouth at one end and discharge portion at the other end, said discharge portion being removably attachable to said container to establish fluid communication between said funnel and said container;
a cap for removably covering the container opening; and
a short base remote from said funnel and having a top which includes a recess for receiving the closed end of said container to support at least a portion of said container above said base, said container being the sole structural interconnection between said funnel and base, said base including a chamber with an opening at its lower end, and means mounted within said chamber for releasbly gripping the periphery of said cap including a plurality of radial projections spaced about said chamber and extending inwardly from the wall of said chamber to grip the periphery of said cap with the inside of said cap facing said chamber opening to enable said cap to engage and cover the open end of the container when said container is introduced generally axially into said base and be properly seated on and removed by said container without direct handling when said container is withdrawn from said base.

* * * * *